United States Patent [19]
Kantor

[11] Patent Number: 6,051,258
[45] Date of Patent: Apr. 18, 2000

[54] PROTEINOID EMULSIONS AND METHODS FOR PREPARATION AND USE THEREOF

[75] Inventor: Martin L. Kantor, Mamaroneck, N.Y.

[73] Assignee: Emisphere Technologies, Inc., Tarrytown, N.Y.

[21] Appl. No.: 08/475,885

[22] Filed: Jun. 7, 1995

[51] Int. Cl.⁷ ............................................... A61K 9/107
[52] U.S. Cl. .................... 424/491; 424/489; 424/499; 514/937; 514/975
[58] Field of Search ................. 424/491, 489, 424/499; 514/937, 975, 2, 773; 516/DIG. 4, DIG. 6; 530/317, 345, 350, 370, 378

[56] References Cited

U.S. PATENT DOCUMENTS

| | | |
|---|---|---|
| Re. 24,899 | 11/1960 | Green . |
| 2,671,451 | 3/1954 | Bolger ..................................... 128/260 |
| 2,717,263 | 9/1955 | McKinney et al. ....................... 560/39 |
| 2,781,384 | 2/1957 | Mannheimer ............................. 554/47 |
| 2,862,918 | 12/1958 | Meyer et al. ....................... 260/123.5 |
| 2,868,740 | 1/1959 | Luce .......................................... 260/8 |
| 2,971,916 | 2/1961 | Schleicher et al. .................... 252/62.5 |
| 3,016,308 | 1/1962 | Macaulay ................................ 177/37 |
| 3,052,655 | 9/1962 | Fox et al. ................................. 260/78 |
| 3,057,344 | 10/1962 | Abella et al. .............................. 128/2 |
| 3,076,790 | 2/1963 | Fox et al. ................................. 260/78 |
| 3,170,802 | 2/1965 | Fukushima .............................. 99/145 |
| 3,190,837 | 6/1965 | Brynko et al. .......................... 252/316 |
| 3,265,682 | 8/1966 | Urs Gloor et al. ..................... 530/330 |
| 3,474,777 | 10/1969 | Figge et al. ................................ 128/2 |
| 3,491,093 | 1/1970 | Pachter et al. ....................... 260/247.5 |
| 3,565,559 | 2/1971 | Sato .......................................... 424/37 |
| 3,567,650 | 3/1971 | Bakan ..................................... 252/316 |
| 3,574,832 | 4/1971 | Engel et al. ............................ 424/183 |
| 3,576,758 | 4/1971 | Emrick .................................... 252/316 |
| 3,598,859 | 8/1971 | Yates et al. ............................... 560/43 |
| 3,687,926 | 8/1972 | Arima et al. ............................ 530/329 |
| 3,725,113 | 4/1973 | Chang ...................................... 117/82 |
| 3,748,277 | 7/1973 | Wagner ................................... 252/316 |
| 3,794,561 | 2/1974 | Matsukawa et al. ................. 195/29 R |
| 3,795,739 | 3/1974 | Birkmayer et al. .................... 424/274 |
| 3,816,404 | 6/1974 | Kablaoui et al. . |
| 3,822,348 | 7/1974 | Higashi et al. ........................... 424/95 |
| 3,849,550 | 11/1974 | Teitelbaum ................................ 424/78 |
| 3,933,873 | 1/1976 | Love et al. . |

(List continued on next page.)

FOREIGN PATENT DOCUMENTS

| | | |
|---|---|---|
| 1077842 | 8/1976 | Canada ............................ A61K 9/50 |
| 0 000 667 A1 | 2/1979 | European Pat. Off. ......... A61K 9/50 |
| 0 036 145 A1 | 9/1981 | European Pat. Off. ....... A61K 31/62 |
| 0 068 314 | 1/1983 | European Pat. Off. . |
| 0 105 804 | 4/1984 | European Pat. Off. ........ C12N 15/00 |
| 0 130 162 A2 | 1/1985 | European Pat. Off. ......... B01J 13/02 |
| 0 170 540 A1 | 2/1986 | European Pat. Off. ......... A61K 9/52 |
| 226223-A2 | 6/1987 | European Pat. Off. ...... C07C 103/46 |
| 0 342 054 A2 | 11/1989 | European Pat. Off. ......... A61K 7/06 |
| 0 342 056 A2 | 11/1989 | European Pat. Off. ......... A61K 7/06 |
| 0 365 183 | 4/1990 | European Pat. Off. ....... A61K 31/18 |
| 0 366 277 | 5/1990 | European Pat. Off. ....... A61K 9/107 |
| 0 418 642 | 3/1991 | European Pat. Off. . |
| 0 448 057 | 9/1991 | European Pat. Off. ........ C12P 21/08 |
| 0 452 161 | 10/1991 | European Pat. Off. ......... A61K 7/48 |
| 0 459 795 | 12/1991 | European Pat. Off. ....... A61K 37/02 |
| 0 467 389 | 1/1992 | European Pat. Off. ......... A61K 9/52 |
| 0 490 549 A1 | 6/1992 | European Pat. Off. ....... A61K 47/12 |
| 0 517 211 A1 | 9/1992 | European Pat. Off. ....... A61K 47/12 |
| 0 616 799 A1 | 9/1994 | European Pat. Off. ......... A61K 7/00 |
| 1 351 358 | 3/1964 | France . |
| 1 468 601 | 2/1967 | France . |
| 2 133 926 | 12/1972 | France ........................... A61K 27/00 |
| 2 326 934 | 5/1977 | France ........................... A61K 47/00 |
| 2 565 102 | 12/1985 | France ............................. A61K 9/52 |
| 2 424 169 | 12/1974 | Germany ......................... A61K 9/00 |
| 2343037 | 3/1975 | Germany . |
| 3 202 255 | 10/1982 | Germany ....................... C08L 89/00 |
| 3 612 102 | 10/1986 | Germany ....................... C07K 15/00 |
| 71258/2 | 12/1987 | Israel . |

(List continued on next page.)

OTHER PUBLICATIONS

Kondo, *Microcapsule Processing and Technology*, pp. 154–165, 1979.
Pastores et al., *Journal of Liquid Chromatography*, 18:3049–3059, 1995.
Sinha et al., *Journal of Biological Chemistry*, 260:10714–10719, 1985.
Chemical Abstracts, 99(23):191473h, Dec. 5, 1983.
Chemical Abstracts, Registry No. 73548–12–6 (Apr. 1991).
Chemical Abstracts, Registry No. 70204–54–5 (Apr. 1991).
G. Picciola, *Il Farmaco*, 31:655–664 (1976).
Franssen et al., J. Med. Chem., 35:1246–1259, 1992.
McCutcheon's Emulsifiers & Detergents International, 1993, vol. 1, pp. 5, 14, 21, 32, 60, 61, 63, 74, 77, 83, 86, 88, 114, 116–119, 134, 142, 191.
Douglas et al., *Chemistry and Industry*, 22:752–756, 1985.
Finch, *Chemistry and Industry*, 22:752–756, 1985.
Butera et al., *J. Med. Chem.*, 34:3212–3228, 1990.
Cimini et al., *Ann. Rept. in Med. Chem.*, 27:89–98, 1992.
Earley et al., *Brain Research*, 546:282–286, 1991.
Ellingboe et al., *J. Med. Chem.*, 35:705–716, 1992.
Lumma et al., *J. Med. Chem.*, 30:758–763, 1987.

(List continued on next page.)

*Primary Examiner*—Robert H. Harrison
*Attorney, Agent, or Firm*—Darby & Darby

[57] ABSTRACT

The present invention provides emulsions, and a method for preparing emulsions, comprising (A) an aqueous phase, (B) an non-aqueous phase, and (C) (i) a proteinoid emulsifier, (ii) a modified hydrolyzed vegetable protein emulsifier wherein said modified hydrolyzed vegetable protein is modified with an amine reactive modifying agent, (iii) an acylated non-α-amino acid emulsifier, (iv) an acylated poly amino acid emulsifier, (v) an acylated peptide emulsifier, (vi) a sulfonated non-α-amino acid emulsifier, (vii) a sulfonated poly amino acid emulsifier, (viii) a sulfonated peptide emulsifier, or (ix) any combination of any of (i), (ii), (iii), (iv), (v), (vi), (vii), and (viii). The proteinoids, modified hydrolyzed vegetable proteins, modified non-α-amino acids, modified poly amino acids, and modified peptides used in the present invention provide emulsions having improved stability against degradation and/or decomposition.

26 Claims, No Drawings

U.S. PATENT DOCUMENTS

| | | | |
|---|---|---|---|
| 3,937,668 | 2/1976 | Zolle | 252/316 |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 3,976,773 | 8/1976 | Curran | 424/250 |
| 4,035,507 | 7/1977 | Bodor et al. | 424/311 |
| 4,048,268 | 9/1977 | Ludwig | 264/15 |
| 4,061,466 | 12/1977 | Sjoholm et al. | 23/230 B |
| 4,117,801 | 10/1978 | Dannelly et al. | 118/20 |
| 4,147,767 | 4/1979 | Yapel | 424/22 |
| 4,183,849 | 1/1980 | Hansen | 260/112.7 |
| 4,199,561 | 4/1980 | Roth et al. | 424/32 |
| 4,217,370 | 8/1980 | Rawlings et al. | 426/98 |
| 4,239,635 | 12/1980 | Rieder . | |
| 4,272,506 | 6/1981 | Schwarzberg | 424/8 |
| 4,289,759 | 9/1981 | Heavner et al. | 424/177 |
| 4,345,588 | 8/1982 | Widder et al. | 128/1.3 |
| 4,348,384 | 9/1982 | Horikoshi et al. | 424/101 |
| 4,351,337 | 9/1982 | Sidman | 128/260 |
| 4,352,883 | 10/1982 | Lim | 435/178 |
| 4,357,259 | 11/1982 | Senyei et al. | 252/316 |
| 4,388,304 | 6/1983 | Nyeki et al. | 424/177 |
| 4,393,192 | 7/1983 | Curatolo et al. . | |
| 4,402,856 | 9/1983 | Schnoring et al. | 428/402.22 |
| 4,405,598 | 9/1983 | Brown | 424/45 |
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,460,563 | 7/1984 | Calanchi | 424/35 |
| 4,462,839 | 7/1984 | McGinley et al. | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,690,786 | 9/1987 | Ninomiya et al. . | |
| 4,692,284 | 9/1987 | Braden . | |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,757,066 | 7/1988 | Shiokari et al. | 514/210 |
| 4,766,012 | 8/1988 | Valenti | 437/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 424/433 |
| 4,878,942 | 11/1989 | Motegi et al. . | |
| 4,886,663 | 12/1989 | Houghten | 424/88 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/12 |
| 4,908,233 | 3/1990 | Takizawa et al. . | |
| 4,919,939 | 4/1990 | Baker | 424/493 |
| 4,925,673 | 5/1990 | Steiner | 424/455 |
| 4,927,928 | 5/1990 | Shroot et al. . | |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,019,400 | 5/1991 | Gombotz et al. . | |
| 5,023,374 | 6/1991 | Simon . | |
| 5,039,481 | 8/1991 | Pacifici et al. | 422/4 |
| 5,055,300 | 10/1991 | Gupta | 424/409 |
| 5,066,487 | 11/1991 | Morelle et al. | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 424/80 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 424/70 |
| 5,250,236 | 10/1993 | Gasco | 264/4.4 |
| 5,271,934 | 12/1993 | Goldberg et al. . | |
| 5,271,961 | 12/1993 | Mathiowitz et al. | 427/213.31 |
| 5,278,148 | 1/1994 | Branca et al. | 514/19 |
| 5,328,992 | 7/1994 | Peter et al. | 534/116 |
| 5,352,461 | 10/1994 | Feldstein et al. | 424/493 |
| 5,384,133 | 1/1995 | Boyes et al. | 424/501 |
| 5,389,377 | 2/1995 | Chagnon et al. . | |
| 5,389,379 | 2/1995 | Dirix et al. | 424/451 |
| 5,418,010 | 5/1995 | Janda et al. | 427/213.31 |
| 5,536,813 | 7/1996 | Charpenel et al. | 530/324 |
| 5,578,323 | 11/1996 | Milstein et al. . | |
| 5,601,846 | 2/1997 | Milstein et al. . | |
| 5,693,338 | 12/1997 | Milstein . | |
| 5,705,529 | 1/1998 | Matyus et al. . | |
| 5,709,861 | 1/1998 | Santiago et al. . | |
| 5,714,167 | 2/1998 | Milstein et al. . | |
| 5,750,147 | 5/1998 | Kantor . | |
| 5,904,936 | 5/1999 | Huille et al. | 424/489 |

FOREIGN PATENT DOCUMENTS

| | | | |
|---|---|---|---|
| 48-24246 | of 1973 | Japan . | |
| 56-68612 | 6/1981 | Japan | A61K 31/19 |
| 58-35111 | of 1983 | Japan | A61K 9/66 |
| 6-107682 | 4/1994 | Japan . | |
| 280825 | 12/1964 | Netherlands . | |
| 280826 | 12/1964 | Netherlands . | |
| 146698 | 11/1982 | Norway | A61K 37/26 |
| 1236885 | of 0000 | United Kingdom . | |
| 929401 | 6/1963 | United Kingdom . | |
| 1075952 | 8/1967 | United Kingdom . | |
| 1404814 | 9/1975 | United Kingdom . | |
| 1 567 763 | 5/1980 | United Kingdom | A61K 9/22 |
| 2 095 994 | 10/1982 | United Kingdom . | |
| WO 85/02772 | of 0000 | WIPO | A61K 49/00 |
| WO 85/00105 | 1/1985 | WIPO | A61K 9/52 |
| WO85/00110 | 1/1985 | WIPO | A61K 47/00 |
| WO 87/04076 | 7/1987 | WIPO | A61K 45/02 |
| WO 88/01213 | 2/1988 | WIPO | B23B 5/16 |
| WO 92/19263 | 12/1992 | WIPO | A61K 39/00 |
| WO 93/18754 | 9/1993 | WIPO | A61K 9/16 |
| WO 93/25583 | 12/1993 | WIPO | C07K 15/00 |
| WO 94/14420 | 7/1994 | WIPO | A61K 9/16 |
| WO 94/18950 | 9/1994 | WIPO | A61K 09/127 |
| WO 94/18997 | 9/1994 | WIPO | A61K 37/00 |
| WO 94/21234 | 9/1994 | WIPO | A61K 7/00 |
| WO 94/23702 | 10/1994 | WIPO | A61K 9/16 |
| WO 94/23767 | 10/1994 | WIPO | A61L 9/16 |
| WO 94/24291 | 10/1994 | WIPO | A61K 39/015 |
| WO 94/28878 | 12/1994 | WIPO | A16K 9/14 |
| WO 95/11690 | 5/1995 | WIPO | A61K 37/00 |
| WO 96/12473 | 5/1996 | WIPO . | |
| WO 96/12474 | 5/1996 | WIPO . | |

| | | |
|---|---|---|
| WO 96/12475 | 5/1996 | WIPO . |
| WO 96/21464 | 7/1996 | WIPO . |
| WO 96/33699 | 10/1996 | WIPO . |
| WO/96/30036 | 10/1996 | WIPO . |
| WO 96/39835 | 12/1996 | WIPO . |
| WO 96/40070 | 12/1996 | WIPO . |
| WO 96/40076 | 12/1996 | WIPO . |
| WO 97/47288 | 12/1997 | WIPO . |

OTHER PUBLICATIONS

Lynch et al., *J. Pharm. and Exp. Therap.*, 269:541–554, 1994.
Matsuno et al., *Brain Research*, 575:315–319, 1992.
Morgan et al., *J. Med. Chem.*, 33:1091–1097, 1990.
Oinuma et al., *J. Med. Chem.*, 33:903–905, 1990.
Rao et al., *Molecular Pharmacology*, 37:978–982, 1990.
*Chemical Abstracts*, 76(14):72994u, (1971).
*Chemical Abstracts*, 84(7):44660d, (1975).
*Chemical Abstracts*, 86(16):107529g, (1976).
*Chemical Abstracts*, 112(15):134663h, (1989).
*Chemical Abstracts*, 114(22):214519x, (1990).
J. Györe et al., Thermal Analysis, vol. 2—Proceedings Fourth ICTA Budapest 1974, p. 387–394.
*Chemical Abstracts*, 99(19) 158832b, (1982).
Derwent Abstracts, JP 67008622, (1967).
Airaudo, C.B. et al. (1987) *Journal of Food Science*, vol. 52(6), pp. 1750–1752.
Andini, S. et al. (1975) *Origins of Life*, vol. 6, pp. 147–153.
Brooke, S. 1 et al. (1977) *BioSystems*, vol. 9, pp. 1–22.
Chen et al. (1975) "Evidence for Hemiacetal Formation", *Biochemistry*, vol. 18, No. 5, pp. 921–925.
Davis et al. (1983) "Leucinal Inhibits . . . ", *Pharmacology Biochemistry Behavior*, vol. 19, pp. 791–794.
Dose, K. (1974) *Origins of Life*, vol. 5, pp. 239–252.
Fasman et al. (1964) *Biochemistry*, vol. 3, No. 11, pp. 1665–1674.
Fox, S.W. et al. (1976) *BioSystems*, vol. 8, pp. 40–44.
Fox, S.W. et al., *Molecular Evolution and the Origin of Life*, Maxel Decker, New York (1977).
Fox, S.W. et al. (1968) *Biochim. Biophys. Acta*, vol. 160, pp. 246–249.
Fox, S.W. (1976) *Origins of Life*, vol. 7, pp. 49–68.
Fox, S.W. (1980) *Naturwissenschaften*, vol. 67, pp. 378–383.
Fox, S.W. et al. (1960) *Archives of Biochemistry and Biophysics*, vol. 86, pp. 281–285.
Fox, S.W. et al. (1974) *Origins of Life*, vol. 5, pp. 227–237.
Fox, S.W. (1984) *Origins of Life*, vol. 14, pp. 485–488.
Gol'dovskii, A.M. (1978) *Zhurnal Evolyutsionnoi Biokhimii i Fiziologii*, vol. 14(6), pp. 437–439.
Gurrieri, S. et al. (1973) *Thermochimica Acta*, vol. 7, pp. 231–239.
Harada, K. et al. (1979) *BioSystems*, vol. 11, pp. 47–53.
Harada et al., (1960) *Archives of Biochemistry and Biophysics*, vol. 86, pp. 274–280.
Hare (1970) *Etude Cenetique De La Polycondensation Thermique D'$_\chi$–Amino Acides*, vol. 45, pp. 330–339.
Heinrich, M.R. et al. (1969) *Archives of Biochemistry and Biophysics*, vol. 130, pp. 441–448.
Heinz, B. et al. (1981) *BioSystems*, vol. 14, pp. 33–40.
Hennon, G. et al. (1975) *Biochimie*, vol. 57, pp. 1395–1396.
Hsu, L.L. et al. (1976) *BioSystems*, vol. 8, pp. 89–101.
Hsu, L.L. et al. (1971) *Currents in Modern Biology*, vol. 4, pp. 12–25.
Ishima, Y. et al. (1981), *BioSystems*, vol.14, pp. 243–251.
Jackson et al. (1991) "Pharmacological . . . ", *J. Pharm. & Exp. Thera.*, vol. 261, No. 1, pp. 546–552.
Jungck, J.R. et al. (1973) *Naturwissenschaften*, vol. 60, pp. 425–427.
Kokufuta, E. et al. (1984) *BioSystems*, vol. 16, pp. 175–181.
Krampitz, G. et al. (1967) *Naturwissenschaften*, pp. 516–517.
Krampitz, G. et al. (1968) *Naturwissenschaften*, pp. 345 and 346.
Krampitz, G. et al. (1966) *Naturwissenschaften*, pp. 7 and 8.
Lacey, Jr., J.C. et al. (1979) *BioSystems*, vol. 11, pp. 1–7 and 9–17.
Lacey, Jr., J.C. et al. (1979) *BioSystems*, vol. 11, pp. 1–7.
Martinez Luque–Romero, M. et al. (1986) *BioSystems*, vol. 19, pp. 267–272.
Masinovsky, Z. et al. (1989) *BioSystems*, vol. 22, pp. 305–310.
Matsuno, K. (1982) *BioSystems*, vol. 15, pp. 1–11.
Matsuno, K. (1984) *BioSystems*, vol. 17, pp. 11–14.
Matsuno, K. (1981) *BioSystems*, vol. 14, pp. 163–170.
McAlhaney, W.W. et al. (1976) *BioSystems*, vol. 8, pp. 45–50.
Melius, P. et al. (1987) *BioSystems*, vol. 20, pp. 213–217.
Melius, P. et al. (1975) *Bioorganic Chemistry*, vol. 4, pp. 385–391.
Melius, P. (1979) *BioSystems*, vol. 11, pp. 125–132.
Miquel, J. et al. (1971) *Currents in Modern Biology*, vol. 3, pp. 299–306.
Nakashima, T. et al. (1980) *J. Mol. Evol.*, vol. 15, pp. 161–168.
Nakashima, T. et al. (1981) *BioSystems*, vol. 14, pp. 151–161.
Novak, V.J.A. (1984) *Origins of Life*, vol. 14, pp. 513–522.
Olafsson, P.G. et al. (1971) *Polymer Letters*, vol. 9, pp. 521–528.
Phillips, R.D. et al. (1974) *Int. J. Peptide Protein Res.*, vol. 6, pp. 309–319.
Przybylski, A.T. et al. (1982) *Die Naturwissenschaften*, vol. 69, pp. 561–563.
Przybylski, A.T. et al. (1984) *Applied Biochemistry and Biotechnology*, vol. 10, pp. 301–307.
Przybylski, A.T. (1985) *BioSystems*, vol. 17, pp. 281–288.
Rohlfing, D.L. (1975) *Origins of Life*, vol. 6, pp. 203–209.
Rohlfing, D.L. (1970) *Science*, vol. 169, pp. 998–1000.
Rohlfing, D.L. (1967) *Archives of Biochemistry and Biophysics*, vol. 118, pp. 468–474.
Rohlfing, D.L. et al. *Catalytic Activities of Thermal Polyanhydro–α–Amino Acids*, pp. 373–418.
Rohlfing, D.L. et al. (1976) *BioSystems*, vol. 5, pp. 139–145.
Ryan, J.W. et al. (1973) *BioSystems*, vol. 5, pp. 115–118.
Saunders, M.A. et al. (1974) *BioSystems*, vol. 6, pp. 81–92.
Snyder, W.D. et al. (1975) *BioSystems*, vol. 7, pp. 222–229.
Sokol, P.E. (1974) *Journal of the American Oil Chemists'Society*, vol. 52, pp. 101–102.
Tschager et al. (1988) *Milchwirtschaftliche Berichte*, vol. 95, pp. 79–83.
Vaughan, G. et al. (1987) *BioSystems*, vol. 20, pp. 219–223.
Vol'kenshtein, M.V. (1989) *Molekulyarnaya Biologiya*, vol. 23(1), pp. 23–37.
Waehneldt, T.V. et al. (1968) *Biochim. Biophys. Acta*, vol. 160, pp. 239–245.
Williams et al. (1991) *J. Biol. Chem.*, vol. 266, No. 8, pp. 5182–5190.
Yuki, A. et al. (1969) *Biochemical and Biophysical Research Communications*, vol. 36(4), pp. 657–663.

Zulaski et al. (1983) "New Carboxyalkyl Inhibitors of Brain Enkenphalinase", *J. Med. Chem.*, 26, pp. 60–65.

(1985) *Chemical Abstracts*, vol. No. 105(1), Abstract No. 12027p.

(1985) *Chemical Abstracts*, vol. No. 102(6), Abstract No. 50870d.

Chemical Abstract, vol. 80(9) Abst. No. 52392a.

Bergeron, Raymond J., et al. (1994) "Macromolecular Self–Assembly of Diketopiperazine Tetrapeptides", *Journal of the American Chemical Society*, vol. 116, pp. 8479–8484.

Bergeron, Raymond J., et al. (1993) "A Comparative Study of the Iron–Clearing Properties of Desferrithiocin Analogues With Desferrioxamine B in a Cebus Monkey Model", *Blood*, vol. 81, No. 8, pp. 2166–2173.

Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood*, vol. 79, No. 7, pp. 1882–1890.

Bergeron, Raymond J., et al. (1991) "Evaluation of Desferrithiocin and Its Synthetic Analogs as Orally Effective Iron Chelators", *Journal of Medicinal Chemistry*, vol. 34, No. 7, pp. 2072–2078.

Bergeron, Raymond et al., "A Comparative Evaluation of Iron Clearance Models", *Annals New York Academy of Sciences*, pp. 378–393.

Andriuoli, G., et al. (1990), *Haemostasis* 20 (suppl. 1):154–158.

Caramazza, I., et al. (1991), *Thrombosis Research* 62:785–789.

Guarini, S., et al. (1983), *Experimentia* 41:350–352.

Guarini, S., et al. (1985), *Pharamcological Research Communications* 17(8):685–697.

Dal Pozzo, A., et al. (1989), *Thrombosis Research* 56:119–124.

Airaudo, C.B., et al. (1987), *Journal of Food Science* 52(6):1750–1752.

Gelb, R., et al (1983), *Lite Sciences* 33(1):83–85.

Watterberg et al. (1988), *Pediatric Research*, vol. 23, No. 4, part 2, p. 570A, col. 1, abstract No. 2209.

Bernstein (1985), *Chest* 87(1):68S–73S.

Damage et al. (1988), *Diabetes* 37:246–251.

184358, *Chemical Abstracts*:83 (1975).

Amino, Y., et al., *Chem. Pharm. Bull.* 36(11):4426–4434 (1988).

Baughman, R.A. et al., *Proc. of the 6th Inter'l. Symp. on Recent Advs. in Drug Delivery Systems, Ctr. for Controlled Chem. Delivery, University of Utah*, Feb. 22–25, 1993, Salt Lake City, UT, pp. 179–180 "Method for Assessing The Stability of Proteinoid Microspheres".

Haas, S. et al., "Assessment Of Stability Of Proteinoid Microspheres", *Proceed. Intern. Symp. Control. Rel. Bioact. Mater.*, 20 (1993), Controlled Release Society, Inc.

X. Ma, et al., *Proceed. Intern. Symp. Control. Rel. Bioact. Mater.*, 20 (1993), Controlled Release Society, Inc. "In Vitro Mechanistic Investigation of the Proteinoid Microsphere Oral Delivery System".

Yen, H.–R H., et al., "Adsorption of Sulforhodamine 101 on Proteinoid Microspheres" *Proceed. Intern. Symp. Control. Rel. Bioact. Mater.*, 20 (1993), Controlled Release Society, Inc.

Presented at "*IBC Rational Drug Design Conference*", San Diego, Calif.—Dec. 1994.

Bergeron, Raymond J. et al., *J. Am. Chem. Soc. 1994*, 116,8479–8484 "Macromolecular Self–Assembly of Diketopiperazine Tetrapeptides".

Leone–Bay et al., Presented at "*Winter Conference on Medicinal and Bioorganic Chemistry*" Steamboat Springs, Colorado—Feb. 1995 "Microsphere Formation and Drug Delivery in a Series of Derivatized Amino Acids".

Santiago et al., *Pharm. Res.* 11: 1994, p. S–298 "Oral Delivery of Heparin Microspheres made with Modified Amino Acids".

Leone–Bay et al., *Pharm. Res.* 11: 1994, p. S–121 "Oral Delivery of Heparin using Acylated Amino Acids".

Sarubbi et al., *Pharm. Res.* 11:1994, p. S–299 "Oral Calcitonin Delivery using the PODDS Technology".

Leipold et al., *Pharm. Res.* 11: 1994, p. S–298 "Oral Delivery of Interferon in Rats and Primates".

Santiago et al., *Pharm. Res.* 11: 1994, p. S–298 "Evaluation in Rats of Vehicles for the Oral Delivery of Low Molecular Weight Heparin".

X. Ma et al., PDD 7303 *Pharmaceutical Research* 9(10):S–244, 1992 (Oct. Supplement).

Milstein et al., Symposia Abstracts. AAPS Annual Meeting, San Antonia, TX, Nov. 15–19, 1993.

Santiago et al. "Initial Studies In The Assessment of Proteinoid Microsphere Activity" *Proceed. Intern. Symp. Control. Rel. Bioact. Mater.*, 20 (1993), Controlled Release Society, Inc.

Santiago et al. "Oral Immunization of Rats with Influenza Virus M Protein (M1) Microspheres" *Proceed. Intern. Symp. Control. Rel. Bioact. Mater.*, 19 (1992), Controlled Release Society, Inc., p. 116–117.

Santiago et al. "Proteinoid Microspheres For The Oral Delivery of Heparin" *Proceed. Intern. Symp. Control. Rel. Bioact. Mater.*, 19 (1992), Controlled Release Society, Inc. p. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater.*, 19 (1992), Controlled Release Society, Inc. p. 516–517.

Doris K. Chiappetta, *Eastern Analytical Symposium*, Nov. 17, 1992 "Solutions for Problems in Bioanalysis".

Elizabeth A. Harris. M.S., *Eastern Analytical Symposium*, Nov. 17, 1992 "Solutions for Problems in Bioanalysis".

*AAPS 6TH Ann. Meeting and Expo.*,"Proteinoids—A Novel Drug Delivery System" Nov. 19, 1992, p. 33.

Milstein et al., "Efficient Oral Delivery Of Monoclonal Antibodies By Proteinoid Encapsulation" *The 1993 Miami Bio/Technology Winter Symposium—Advances in Gene Technology: Protein Engineering and Beyond*, Jan. 17–22, 1993.

Xinghang Ma, et al. "Stability Study of Drug–loaded Proteinoid Microsphere Formulations during Freeze–drying" *Journal of Drug Targeting*, 1994, vol. 2, pp 9–21.

Baughman et al., "Screening Candidate Microsphere Formulations By Incubating In Simulated Digestive Fluids" *Proc. of the 6th Intern'l. Sympo. on Recent Advances in Drug Delivery Systems, Ctr. for Controlled Chem. Delivery, University of Utah*, Feb. 22–25, 1993, pp. 181–182.

Robert O. Dillman, M.D., Annals of Internal Medicine 1989:111 pp. 592–600, "Monoclonal Antibodies for Treating Cancer".

Brendan D. Curti, Critical Reviews in Oncology/Hematology, 1993: 14 pp. 29–39 "Physical barriers to drug delivery in tumors".

V. Hird et al, Genes and Cancer, edited by Desmond Carney & Karol Sikora, pp. 183–189, Immunotherapy with Monoclonal Antibodies.

Michael E. Osband et al., Immunology Today, vol. 11, No.6 1990, pp. 93–95, "Problems in the investigational study and clinical use of cancer immunotherapy".

Tibtech Feb. 1993 vol. 11, pp. 42–44 "Therapeutic antibodies—the coming of age".

Thomas A. Waldmann, Articles Jun. 21, 1991, pp. 1657–1662, "Monoclonal Antibodies in Diagnosis and Therapy".

Chemical Abstracts, 99(23):191473h, Dec. 5, 1983.

PROTEINOID EMULSIONS AND METHODS FOR PREPARATION AND USE THEREOF

FIELD OF THE INVENTION

The present invention relates to emulsions and methods for preparing them. These emulsions include proteinoids, modified hydrolyzed vegetable proteins, modified non-α-amino acids, modified poly amino acids, and/or modified peptides as emulsifying agents.

BACKGROUND OF THE INVENTION

Emulsions typically are heterogenous mixtures of two or more immiscible liquid phases wherein at least one liquid forms small droplets suspended in the other liquid(s). Emulsions include a continuous phase and a dispersed phase. Generally, emulsions are either oil-in-water emulsions wherein the water is the continuous phase or water-in-oil emulsions wherein the oil is the continuous phase.

Typically, emulsification requires an emulsifying agent or a surfactant. Generally, emulsifying agents are either (a) polymers which coat the surface of oil-type particles to prevent those particles from coalescing or (b) long-chain alcohols or fatty acids that have solubility properties which reduce the surface tension at the interface of the suspended particles.

The proteinoids, modified hydrolyzed vegetable proteins, modified non-α-amino acids, modified poly amino acids, and modified peptides used in the present invention provide emulsions having improved stability against degradation and/or decomposition.

SUMMARY OF THE INVENTION

The emulsions of the present invention comprise
(A) an aqueous phase,
(B) an non-aqueous phase, and
(C) (i) a proteinoid emulsifier,
   (ii) a modified hydrolyzed vegetable protein emulsifier wherein said modified hydrolyzed vegetable protein is modified with an amine reactive modifying agent,
   (iii) an acylated non-α-amino acid emulsifier,
   (iv) an acylated poly amino acid emulsifier,
   (v) an acylated peptide emulsifier,
   (vi) a sulfonated non-α-amino acid emulsifier,
   (vii) a sulfonated poly amino acid emulsifier,
   (viii) a sulfonated peptide emulsifier, or
   (ix) any combination of any of (i), (ii), (iii), (iv), (v), (vi), (vii), and (viii).

Further, the present invention contemplates a method for preparing the emulsions described above. The method comprises mixing an aqueous phase, a non-aqueous phase, and at least one of the above emulsifiers.

DETAILED DESCRIPTION OF THE INVENTION

The emulsions of the present invention incorporate proteinoid, modified hydrolyzed vegetable protein, modified non-α-amino acid, modified poly amino acid, and modified peptide emulsifiers. These emulsions exhibit good stability in that there is minimal decomposition or degradation of the emulsion over time. The emulsions of the invention incorporate readily available or easy to prepare, inexpensive emulsifiers. The formulation methods of the present invention are cost effective for preparing these compositions, are simple to perform, and are amenable to industrial scale for commercial production.

The emulsions of monomers prepared using the emulsifiers of the invention are suitable for emulsion polymerization. Other uses for the emulsions of the invention include preparation of pharmaceutical dosage forms.

Aqueous Phase

The aqueous phase can be water alone or water and another material in solution. The aqueous phase may optionally contain additives such as stabilizers, phosphate buffer salts, citric acid, acetic acid, and gum acacia. Suitable, but non-limiting, examples of stabilizing additives include gum acacia, gelatin, methyl cellulose, polyethylene glycol, and polylysine. The preferred stabilizing additives are gum acacia, gelatin and methyl cellulose.

Non-aqueous Phase

The non-aqueous phase is a material or combination of materials which is insoluble or only minimally soluble in water. A material or combination of materials is considered insoluble or minimally soluble in water if a mixture of the material(s) with water or an aqueous mixture is not miscible and separates into layers. Typically, one layer contains the water or aqueous mixture and another layer contains the non-aqueous material(s).

The preferred non-aqueous phase materials are organic materials such as solvents, oils, or polymerization monomers. The most preferred organic materials are oils and polymerization monomers.

Examples of organic materials which are useful in the emulsions of the present invention include but are not limited to vegetable oils, such as, for example, soy oil and the like; solvents such as, for example, heptane, mesitylene, diethyl phthalate, and the like; fragrances, such as, for example, limonene, eugenol, β-ionone, ethylphenylacetate and the like. Other useful organic materials include those containing vinyl monomer(s), such as, for example, amine monomers, glycidylether monomers, arylate monomers, or multifunctional monomers. Some preferred monomers include vinyl acetate, butyl acrylate, methyl methacrylate, mixtures thereof, and the like.

Emulsifiers

Proteinoids

Proteinoids are artificial polymers of amino acids. An amino acid is any carboxylic acid having at least one free amine group and includes naturally occurring and synthetic amino acids. Amino acids further include both α- and non-α-amino acids. Many amino acids and amino acid esters are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA).

Representative, but not limiting, amino acids suitable as components of proteinoids have the formula:

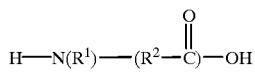

I wherein: $R^1$ is hydrogen, $C_1$–$C_4$ alkyl, or $C_2$–$C_4$ alkenyl;
$R^2$ is $C_1$–$C_{24}$ alkyl, $C_2$–$C_{24}$ alkenyl, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl), or naphthyl ($C_2$–$C_{10}$ alkenyl);

$R^2$ being optionally substituted with $C_1$–$C_4$ alkyl, $C_2$–$C_4$ alkenyl, $C_1$–$C_4$ alkoxy, —OH, —SH, —$CO_2R^3$, $C_3$–$C_{10}$ cycloalkyl, $C_3$–$C_{10}$ cycloalkenyl, heterocyclic having 3–10 ring atoms wherein the hetero atom is one or more of N, O, S, or any combination thereof, aryl, ($C_1$–$C_{10}$ alk)aryl, ar($C_1$–$C_{10}$ alkyl) or any combination thereof;

$R^2$ being optionally interrupted by oxygen, nitrogen, sulfur, or any combination thereof; and $R^3$ is hydrogen, $C_1$–$C_4$ alkyl, or $C_2$–$C_4$ alkenyl.

Preferred naturally occurring amino acids are alanine, arginine, asparagine, aspartic acid, citrulline, cysteine, cystine, glutamine, glycine, glutamic, histidine, isoleucine, leucine, lysine, methionine, ornithine, phenylalanine, proline, serine, threonine, tryptophan, tyrosine, valine, hydroxy proline, γ-carboxyglutamate, phenylglycine, or O-phosphoserine. The preferred amino acids are arginine, leucine, lysine, phenylalanine, tyrosine, tryptophan, valine, and phenylglycine.

Preferred non-naturally occurring amino acids are β-alanine, α-amino butyric acid, γ-amino butyric acid, γ-(aminophenyl) butyric acid, α-amino isobutyric acid, citrulline, ε-amino caproic acid, 7-amino heptanoic acid, β-aspartic acid, aminobenzoic acid, aminophenyl acetic acid, aminophenyl butyric acid, γ-glutamic acid, cysteine, ε-lysine, methionine sulfone, norleucine, norvaline, ornithine, d-ornithine, p-nitro-phenylalanine, hydroxy proline, 1,2,3,4,-tetrahydroisoquinoline-3-carboxylic acid, and thioproline.

The proteinoids useful herein preferably are prepared from mixed amino acids by methods well known in the art. For example, methods for preparing proteinoids are described in U.S. Pat. No. 4,925,673 or International Patent Application No. WO 93/25583.

Preferred proteinoids are condensation polymers, and most preferably, are thermal condensation polymers. These polymers may be directed or random polymers. Proteinoids can be linear, branched, or cyclical, and certain proteinoids can be units of other linear, branched, or cyclical proteinoids.

Preferably, proteinoids contain from about 2 to about 20 amino acid residues, and most preferably from about 2 to about 8 amino acid residues. Preferred proteinoids have a molecular weight which ranges from about 250 to about 2400 daltons, and most preferably from about 250 to about 600. Special mention is made of proteinoids having a molecular weight of from about 250 to about 400 daltons.

Special mention is made of diketopiperazines. Diketopiperazines are six member ring compounds. The ring includes two substituted or unsubstituted nitrogen atoms. Two of the carbon atoms in the ring are each substituted with an oxygen atom, forming carbonyl groups. Preferably, the carbonyl groups are at the 1 and 4 ring positions. These rings can be optionally, and most often are, further substituted on the remaining carbon atoms.

Diketopiperazine ring systems may be generated during thermal polymerization or condensation of amino acids or amino acid derivatives. (Gyore, J; Ecet M. *Proceedings Fourth ICTA* (*Thermal Analysis*), 1974, 2, 387–394 (1974)). These six membered ring systems were presumably generated by intra-molecular cyclization of the dimer prior to further chain growth or directly from a linear peptide (Reddy, A.V., *Int. J. Peptide Protein Res.*, 40, 472–476 (1992); Mazurov, A. A. et al., *Int. J. Peptide Protein Res.*, 42, 14–19 (1993)).

Diketopiperazines can also be formed by cyclodimerization of amino acid ester derivatives as described by Katchalski et al., *J. Amer. Chem. Soc.*, 68, 879–880 (1946), by cyclization of dipeptide ester derivatives, or by thermal dehydration of amino acid derivatives and high boiling solvents as described by Kopple et al., *J. Org. Chem.*, 33 (2), 862–864 (1968).

Diketopiperazines typically are formed from α-amino acids. Preferably, the α-amino acids of which the diketopiperazines are derived are glutamic acid, aspartic acid, tyrosine, phenylalanine, and optical isomers of any of the foregoing.

Special mention is made of diketopiperazines of the formula:

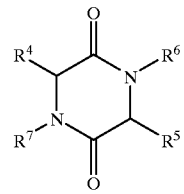

II wherein $R^4$, $R^5$, $R^6$, and $R^7$ independently are hydrogen, $C_1$–$C_{24}$ alkyl, $C_1$–$C_{24}$ alkenyl, phenyl, naphthyl, ($C_1$–$C_{10}$ alkyl)phenyl, ($C_1$–$C_{10}$ alkenyl)phenyl, ($C_1$–$C_{10}$ alkyl)naphthyl, ($C_1$–$C_{10}$ alkenyl)naphthyl, phenyl ($C_1$–$C_{10}$ alkyl), phenyl($C_1$–$C_{10}$ alkenyl), naphthyl ($C_1$–$C_{10}$ alkyl), and naphthyl ($C_1$–$C_{10}$ alkenyl); any of $R^4$, $R^5$, $R^6$, and $R^7$ independently may optionally be substituted with $C_1$–$C_4$ alkyl, $C_1$–$C_4$ alkenyl, $C_1$–$C_4$ alkoxy, —OH, —SH, and —$CO_2R^8$ or any combination thereof; $R^8$ is hydrogen, $C_1$–$C_4$ alkyl or $C_1$–$C_4$ alkenyl; and any of $R^4$, $R^5$, $R^6$, and $R^7$ independently may optionally be interrupted by oxygen, nitrogen, sulfur, or any combination thereof.

The phenyl or naphthyl groups may optionally be substituted. Suitable, but non-limiting, examples of substituents are $C_1$–$C_6$ alkyl, $C_1$–$C_6$ alkenyl, $C_1$–$C_6$ alkoxy, —OH, —SH, or $CO_2R^9$ wherein $R^9$ is hydrogen, $C_1$–$C_6$ alkyl, or $C_1$–$C_6$ alkenyl.

Preferably, $R^6$ and $R^7$ independently are hydrogen, $C_1$–$C_4$ alkyl or $C_1$–$C_4$ alkenyl. Special mention is made of the N-substituted diketopiperazine wherein one or both of the nitrogen atoms is substituted with a methyl group.

Special mention is also made of diketopiperazines of the formula:

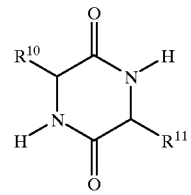

III wherein $R^{10}$ and $R^{11}$ independently are hydrogen, $C_1$–$C_{24}$ alkyl, $C_1$–$C_{24}$ alkenyl, phenyl, naphthyl, ($C_1$–$C_{10}$ alkyl) phenyl, ($C_1$–$C_{10}$ alkenyl)phenyl, ($C_1$–$C_{10}$ alkyl)naphthyl, ($C_1$–$C_{10}$ alkenyl)naphthyl, phenyl ($C_1$–$C_{10}$ alkyl), phenyl ($C_1$–$C_{10}$ alkenyl), naphthyl ($C_1$–$C_{10}$ alkyl), and naphthyl ($C_1$–$C_{10}$ alkenyl); but both $R^{10}$ and $R^{11}$ can not be hydrogen; either or both $R^{10}$ or $R^{11}$ independently may optionally be substituted with $C_1$–$C_4$ alkyl, $C_1$–$C_4$ alkenyl, $C_1$–$C_4$ alkoxy, —OH, —SH, and —$CO_2R^{12}$ or any combination thereof; $R^{12}$ is hydrogen, $C_1$–$C_4$ alkyl or $C_1$–$C_4$ alkenyl; and either or both $R^{10}$ and $R^{11}$ independently may optionally be interrupted by oxygen, nitrogen, sulfur, or any combination thereof.

The phenyl or naphthyl groups may optionally be substituted. Suitable, but non-limiting, examples of substituents are $C_1$–$C_6$ alkyl, $C_1$–$C_6$ alkenyl, $C_1$–$C_6$ alkoxy, —OH, —SH, or $CO_2R^{13}$ wherein $R^{13}$ is hydrogen, $C_1$–$C_6$ alkyl, or $C_1$–$C_6$ alkenyl. When one of $R^{10}$ or $R^{11}$ is hydrogen, the diketopiperazine is mono-carbon-(C)-substituted. When neither $R^{10}$ nor $R^{11}$ is hydrogen, the diketopiperazine is di-carbon-(C)-substituted.

Preferably, $R^{10}$, $R^{11}$, or both $R^{10}$ and $R^{11}$, contain at least one functional group, a functional group being a non-hydrocarbon portion responsible for characteristic reactions of the molecule. Simple functional groups are heteroatoms including, but not limited to halogens, oxygen, sulfur, nitrogen, and the like, attached to, the carbon of an alkyl group by a single or multiple bond. Other functional groups include, but are not limited to, for example, hydroxyl groups, carboxyl groups, amide groups, amine groups, substituted amine groups, and the like.

Preferred diketopiperazines are those which are substituted at one or two of the carbons of the ring with a functional group that includes at least one carboxyl functionality.

Modified Hydrolyzed Vegetable Protein

Modified hydrolyzed vegetable protein is prepared from hydrolyzed vegetable protein. Hydrolyzed vegetable protein is a product which is derived from defatted vegetable meal. In practicing the present invention, acid or enzyme hydrolyzed vegetable proteins are useful. The vegetable proteins generally contain titratable carboxylic acid groups (COOH) ranging from about 3 to about 8 milliequivalents/g, preferably from about 4 to about 6 milliequivalents/g, and total free amino groups ($NH_2$) ranging from about 3 to about 9 milliequivalents/g, preferably ranging from about 4 to about 7 milliequivalents/g $NH_2$. The molecular weight of the hydrolyzed vegetable protein ranges from about 100 daltons to about 2000 Daltons, and preferably from about 200 to about 500 daltons.

Hydrolyzed vegetable protein is available from a variety of commercial sources, such as, for example, Ajinomoto USA, Inc. (Teaneck, N.J.); Central Soya Co., Inc. (Fort Wayne, Ind.); Champlain Industries, Inc. (Clifton, N.J.,); Archer Daniels Midland (Decatur, Ill.), A.E. Staley Company, Gunther Products Division, (Decatur, Ill.), and additional companies listed in "Food Engineering Master", an annual publication of Chilton Co., Radnor, Pa. A preferred hydrolyzed vegetable protein in practicing this invention is available from Ajinomoto USA under the tradename AJI-EKI. This product is an acid hydrolyzed liquid soybean protein which is derived from defatted soybean meal. Other preferred hydrolyzed soy proteins include PROFAM 781, available from Archer Daniels Midland and PRO-TEIN 1550 and MIR-A-FOAM 100 available from A.E. Staley, Gunther Products division.

If desired, a dried protein extract of the hydrolyzed vegetable protein solution may be used to prepare the modified hydrolyzed vegetable protein of the invention. The dried protein extract is preparable by extracting the hydrolyzed vegetable protein solution with a suitable solvent, e.g., methanol, followed by evaporating the solvent extract.

The hydrolyzed vegetable protein is modified by an amine reactive agent. Typically the hydrolyzed vegetable protein is modified by acylating or sulfonating at least one free amine group, with an acylating or sulfonating agent which reacts with at least one of the free amine groups present. Suitable, but non-limiting, examples of acylating or sulfonating agents useful for preparing the modified hydrolyzed vegetable protein emulsifiers of the present invention include acylating and sulfonating agents having the formula:

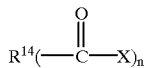

or $R^{14}$—$SO_2$—X wherein $R^{14}$ is alkyl or alkenyl, preferably having from 1 to 20 carbon atoms, or aromatic preferably having from 6 to 20 carbon atoms and n is 1 or 2.

The $R^{14}$ group can be substituted or unsubstituted, The preferred substituents include $C_1$ to $C_4$ alkyl, $C_1$ to $C_4$ alkenyl, $C_1$ to $C_4$ alkoxy, $CO_2R^{15}$ wherein $R^{15}$ is hydrogen, $C_1$ to $C_4$ alkyl or $C_1$ to $C_4$ alkenyl.

Preferably, $R^{14}$ is methyl, ethyl, phenyl, benzyl or naphthyl. More preferably, $R^{14}$ is phenyl, or acetyl. X is a leaving group. In a reaction in which the substrate molecule becomes cleaved, part of it (the part not containing the carbon) is usually called the leaving group. See *Advanced Organic Chemistry*, 2d edition, Jerry March, New York: McGraw-Hill Book (1977), page 187, Typical leaving groups include, but are not limited to, halogens such as chlorine, bromine and iodine.

Examples of the acylating and sulfonating agents for modifying hydrolyzed vegetable protein include, but are not limited to, acyl halides, such as, for example, acetyl chloride, propyl chloride, benzoyl chloride, phthaloyl chloride, hexahydrophthaloyl chloride, tetrahydrophthaloyl chloride, cyclohexanoyl chloride, sebacoyl chloride, hippuryl chloride and the like; sulfonyl halides, such as, for example, benzene sulfonyl chloride, acetylsulfanilyl chloride, and the like; anhydrides, such as, for example, acetic anhydride, propyl anhydride, benzoic anhydride, maleic anhydride, phthalic anhydride, tetrahydrophthalic anhydride, hexahydrophthalic anhydride, hippuric anhydride and the like. The preferred acylating and sulfonating agents are benzoyl chloride, benzene sulfonyl chloride, cyclohexanoyl chloride, phthalic anhydride, tetrahydrophthalic anhydride, and hexahydrophthalic anhydride.

The hydrolyzed vegetable protein is typically modified by first dissolving it in aqueous alkaline solution of a metal hydroxide, e.g., sodium or potassium hydroxide, and heating at the solution to a temperature ranging from about 50° C. to about 70° C., preferably from about 50° C. to about 60° C., for a period ranging from about 10 minutes to about 40 minutes, preferably about 15 minutes. The amount of alkali employed per mmole of titratable $NH_2$ in the hydrolyzed vegetable protein generally ranges from about 2 to about 3 mmole, and preferably from about 2.2 to about 2.5 mmole. The pH of the solution is generally maintained from about 8 to about 13, preferably ranging from about 9 to about 10.

Thereafter, the acylating or sulfonating agent is added to the reaction mixture. The amount of acylating or sulfonating agent in relation to the quantity of hydrolyzed vegetable protein employed is based on the equivalents of total free $NH_2$ in the hydrolyzed vegetable protein. Thus, from about 0.3 to about 1.2 equivalents of acylating or sulfonating agent are used for each molar equivalent of total $NH_2$ groups in the hydrolyzed vegetable protein, and preferably from about 0.6 to about 1.0 equivalent of acylating or sulfonating agent for each molar equivalent of groups $NH_2$ groups in the hydrolyzed vegetable protein. The modified hydrolyzed vegetable protein is then recovered from the reaction mixture using standard techniques, such as, for example, precipitation with dilute acid and filtration of the precipitate. See also PCT Publication No. WO 94/14420; published Jul. 7, 1994.

In an alternative method, the vegetable protein is dissolved in glacial acetic acid by warming the solution to from about 50 to about 90° C. preferably from about 60 to about 75° C. The alkylating agent, preferably an acid anhydride, in molar proportions to react with at least one amino group, is added portionwise over about 30 to about 180 minutes, and preferably from about 40 to about 70 minutes. The mixture is allowed to stir for from about 60 to about 240 minutes, and preferably from about 100 to about 200 minutes at the preferred temperature.

The mixture is then quenched with an excess of water, preferably about 3 to about 5 volumes and the resultant precipitate of modified hydrolyzed vegetable protein is separated from the acetic acid solution by filtration or centrifugation. It is washed with water to remove impurities, converted to the sodium salt, and dried.

Modified Amino Acids

The modified non-α-amino acids, poly amino acids or peptides which are useful for preparing emulsions are either acylated or sulfonated and include non-α-amino acid amides or sulfonamides, and poly amino acid or peptide amides or sulfonamides.

Modified poly amino acids and peptides may include one or more acylated or sulfonated amino acid(s). Although linear modified poly amino acids and peptides used generally include only one modified amino acid, other poly amino acid and peptide configurations can include more than one modified amino acid. Poly amino acids and peptides can be polymerized with the modified amino acid(s) or can be modified after polymerization.

Acylated Non-α-Amino Acids

Acylated non-α-amino acids, poly amino acids, and peptides are modified by acylating at least one free amine group with an acylating agent which reacts with at least one of the free amine groups present.

Preferred acylated non-α-amino acids have the formula:

$$\text{Ar—Y—(R}^{16}\text{)—OH} \quad\quad \text{IV}$$

wherein Ar is a substituted or unsubstituted phenyl or naphthyl;

Y is 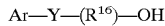, $R^{16}$ has the formula

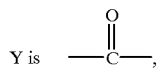, wherein:

$R^{17}$ is $C_2$ to $C_{24}$ alkyl, $C_2$ to $C_{24}$ alkenyl, phenyl, naphthyl, ($C_1$ to $C_{10}$ alkyl) phenyl, ($C_1$ to $C_{10}$ alkenyl) phenyl, ($C_1$ to $C_{10}$ alkyl) naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl ($C_1$ to $C_{10}$ alkyl) and naphthyl ($C_1$ to $C_{10}$ alkenyl);

$R^{17}$ is optionally substituted with $C_1$ to $C_4$ alkyl, $C_1$ to $C_4$ alkenyl, $C_1$ to $C_4$ alkoxy, —OH, —SH and —$CO_2R^{18}$, cycloalkyl, cycloalkenyl, heterocyclic alkyl, alkaryl, heteroaryl, heteroalkaryl, or any combination thereof;

$R^{19}$ is hydrogen, $C_1$ to $C_4$ alkyl or $C_1$ to $C_4$ alkenyl;

$R^{17}$ is optionally interrupted by oxygen, nitrogen, sulfur or any combination thereof; and $R^{18}$ is hydrogen, $C_1$ to $C_4$ alkyl or $C_1$ to $C_4$ alkenyl.

Special mention is also made of those acylated non-α-amino acids having the formula:

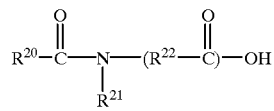

wherein:

$R^{20}$ is (i) $C_3$–$C_{10}$ cycloalkyl, optionally substituted with $C_1$–$C_7$ alkyl, $C_2$–$C_7$ alkenyl, $C_1$–$C_7$ alkoxy, hydroxy, phenyl, phenoxy or —$CO_2R^{23}$, wherein $R^{23}$ is hydrogen, $C_1$–$C_4$ alkyl, or $C_2$–$C_4$ alkenyl; or (ii) $C_1$–$C_6$ alkyl substituted with $C_3$–$C_{10}$ cycloalkyl;

$R^{21}$ is hydrogen, $C_1$–$C_4$ alkyl, or $C_2$–$C_4$ alkenyl;

$R^{22}$ is $C_2$–$C_{24}$ alkyl, $C_2$–$C_{24}$ alkenyl, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl) or naphthyl ($C_2$–$C_{10}$ alkenyl);

$R^{22}$ being optionally substituted with $C_1$–$C_4$ alkyl, $C_2$–$C_4$ alkenyl, $C_1$–$C_4$ alkoxy, —OH, —SH, —$CO_2R^{24}$, $C_3$–$C_{10}$ cycloalkyl, $C_3$–$C_{10}$ cycloalkenyl, heterocycle having 3–10 ring atoms wherein the hetero atom is one or more of N, O, S or any combination thereof, aryl, ($C_1$–$C_{10}$ alk)aryl, ar($C_1$–$C_{10}$ alkyl), or any combination thereof;

$R^{22}$ being optionally interrupted by oxygen, nitrogen, sulfur, or any combination thereof; and $R^{24}$ is hydrogen, $C_1$–$C_4$ alkyl, or $C_2$–$C_4$ alkenyl.

Poly amino acids are either peptides or two or more amino acids linked by a bond formed by other groups which can be linked, e.g. an ester, anhydride, or an anhydride linkage. Special mention is made of non-naturally occurring poly amino acids and particularly non-naturally occurring hetero poly amino acids, i.e. polymers of mixed amino acids.

Peptides are two or more amino acids joined by a peptide bond. Peptides can vary in length from dipeptides with two amino acids to poly peptides with several hundred amino acids. See *Chambers Biological Dictionary*, editor Peter M. B. Walker, Cambridge, England: Chambers Cambridge, 1989, page 215. Special mention is made of dipeptides, tripeptides, tetrapeptides, and pentapeptides.

Acylated non-α-amino acids, poly amino acids, and peptides may be prepared by reacting appropriate single amino acids, mixtures of two or more amino acids, amino acid esters, poly amino acids, poly amino acid esters, or peptide esters with an acylating agent which reacts with free amino moieties present, to form amides.

Suitable, but non-limiting, examples of acylating agents useful in preparing acylated non-α-amino acids, poly amino acids, and peptides include acid chloride acylating agents having the formula

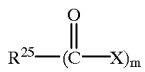

wherein:

R[25] is an appropriate group for the modified amino acid being prepared, such as, but not limited to, alkyl, alkenyl, cycloalkyl, or aromatic, and particularly methyl, ethyl, cyclohexyl, cyclophenyl, phenyl, or benzyl, X is a leaving group and n is 1 or 2. Typical leaving groups include, but are not limited to, halogens such as chlorine, bromine and iodine.

Examples of the acylating agents include, but are not limited to, acyl halides such as, for example, acetyl chloride, propyl chloride, benzoyl chloride, phthaloyl chloride, hexahydrophthaloyl chloride, tetrahydrophthaloyl chloride, cyclohexanoyl chloride, cyclopentanoyl chloride, and cycloheptanoyl chloride, sebacoyl chloride, hippuryl chloride and the like; anhydrides, such as, for example, acetic anhydride, propyl anhydride, benzoic anhydride, cyclohexanoic anhydride, maleic anhydride, phthalic anhydride, tetrahydrophthalic anhydride, hexahydrophthalic anhydride, hippuric anhydride and the like. The preferred acylating agents are benzoyl chloride, cyclohexanoyl chloride, cyclopentanoyl chloride, cycloheptanoyl chloride, phthalic anhydride, tetrahydrophthalic anhydride, and hexahydrophthalic anhydride.

The amine groups can also be modified by the reaction of a carboxylic acid with coupling agents such as the carbodiimide derivatives of amino acids, particularly hydrophilic amino acids such as phenylalanine, tryptophan, and tyrosine. Further examples include dicyclohexylcarbodiimide and the like.

If the non-α-amino acid, poly amino acid, or peptide is multifunctional, i.e. has more than one —OH, —NH$_2$ or —SH group, then it may optionally be acylated at one or more functional groups to form, for example, an ester, amide, or thioester linkage.

For example, in the preparation of many acylated non-α-amino acids, poly amino acids, and peptides the compound is dissolved in an aqueous alkaline solution of a metal hydroxide, e.g., sodium or potassium hydroxide and the acylating agent added. The reaction time can range from about 1 hour and about 4 hours, preferably about 2–2.5 hours. The temperature of the mixture is maintained at a temperature generally ranging between about 50° C. and about 70° C., preferably between about 10° C. and about 50° C. The amount of alkali employed per equivalent of NH$_2$ groups in the non-α-amino acids, poly amino acids, or peptides generally ranges between about 1.25 moles and about 3 moles, and is preferably between about 1.5 moles and about 2.25 moles per equivalent of NH$_2$. The pH of the reaction solution generally ranges between about pH 8 and about pH 13, and is preferably between about pH 10 and about pH 12. The amount of amino modifying agent employed in relation to the quantity of non-α-amino acids, poly amino acids, or peptides is based on the moles of total free NH$_2$ in the amino acids. In general, the amino modifying agent is employed in an amount ranging between about 0.5 and about 2.5 mole equivalents, preferably between about 0.75 and about 1.25 equivalents, per molar equivalent of total NH$_2$ groups in the non-α-amino acid, poly amino acid, or peptide.

The modification reaction is quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded, and modified non-α-amino acids, poly amino acids or peptides are collected by filtration or decantation. The crude modified non-α-amino acids, poly amino acids or peptides are then mixed with water. Insoluble materials are removed by filtration and the filtrate is dried in vacuo. The yield of modified product generally ranges between about 30 and about 60%, and usually about 45%. The present invention also contemplates using non-α-amino acids, poly amino acids and peptides which have been modified by multiple acylation, e.g., diacylation or triacylation as emulsifiers.

If esters or amides are the starting materials, they are dissolved in a suitable organic solvent such as dimethylformamide or pyridine, are reacted with the amine modifying agent at a temperature ranging between about 5° C. and about 70° C., preferably about 25° C., for a period ranging between about 7 and about 24 hours. The amount of amine modifying agents used relative to the non-α-amino acid esters, poly amino acid esters, and peptide esters are the same as described above for the acids.

Thereafter, the reaction solvent is removed under negative pressure and optionally the ester or amide functionality can be removed by hydrolyzing the modified ester with a suitable alkaline solution, e.g., 1N sodium hydroxide, at a temperature ranging between about 50° C. and about 80° C., preferably about 70° C., for a period of time sufficient to hydrolyze off the ester group and form the modified non-α-amino acid, poly amino acid, or peptide having a free carboxyl group. The hydrolysis mixture is then cooled to room temperature and acidified, e.g., with an aqueous 25% hydrochloric acid solution, to a pH ranging between about 2 and about 2.5. The modified compound precipitates out of solution and is recovered by conventional means such as filtration or decantation.

The modified compounds may be purified by acid precipitation, recrystallization or by fractionation on solid column supports. Fractionation may be performed on a suitable solid column supports such as silica gel, alumina, using solvent mixtures such as acetic acid/butanol/water as the mobile phase; reverse phase column supports using trifluoroacetic acid/acetonitrile mixtures as the mobile phase; and ion exchange chromatography using water as the mobile phase. The modified compounds may also be purified by extraction with a lower alcohol such as methanol, butanol, or isopropanol to remove impurities such as inorganic salts.

The modified non-α-amino acids, poly amino acids, and peptides generally are soluble in alkaline aqueous solution (pH≦9.0); partially soluble in ethanol, n-butanol and 1:1 (v/v) toluene/ethanol solution and insoluble in water. The alkali metal salts, e.g., the sodium salt of the modified non-α-amino acids, poly amino acids, and peptides are generally soluble in water at about a pH of 6–8.

In poly amino acids or peptides, one or more of the amino acids may be acylated. Modified poly amino acids and peptides may include one or more acylated amino acid(s). Although linear modified poly amino acids and peptides will generally include only one acylated amino acid, other poly amino acid and peptide configurations can include more than one acylated amino acid. Poly amino acids and peptides can be polymerized with the acylated amino acid(s) or can be acylated after polymerization.

Sulfonated Amino Acids

Sulfonated non-α-amino acids, poly amino acids, and peptides are modified by sulfonating at least one free amine group with a sulfonating agent which reacts with at least one of the free amine groups present.

Special mention is made of compounds of the formula

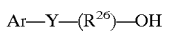    VI wherein Ar is a substituted or unsubstituted phenyl or naphthyl;

Y is —SO$_2$—, R$^{26}$ has the formula

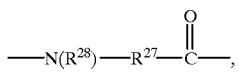

wherein:
R$^{27}$ is C$_2$ to C$_{24}$ alkyl, C$_2$ to C$_{24}$ alkenyl, phenyl, naphthyl, (C$_1$ to C$_{10}$ alkyl) phenyl, (C$_1$ to C$_{10}$ alkenyl) phenyl, (C$_1$ to C$_{10}$ alkyl) naphthyl, (C$_1$ to C$_{10}$ alkenyl) naphthyl, phenyl (C$_1$ to C$_{10}$ alkyl), phenyl (C$_1$ to C$_{10}$ alkenyl), naphthyl (C$_1$ to C$_{10}$ alkyl) and naphthyl (C$_1$ to C$_{10}$ alkenyl);

R$^{27}$ is optionally substituted with C$_1$ to C$_4$ alkyl, C$_1$ to C$_4$ alkenyl, C$_1$ to C$_4$ alkoxy, —OH, —SH and —CO$_2$R$^{29}$ or any combination thereof;

R$^{29}$ is hydrogen, C$_1$ to C$_4$ alkyl or C$_1$ to C$_4$ alkenyl;

R$^{27}$ is optionally interrupted by oxygen, nitrogen, sulfur or any combination thereof; and R$^{28}$ is hydrogen, C$_1$ to C$_4$ alkyl or C$_1$ to C$_4$ alkenyl.

Suitable, but non-limiting, examples of sulfonating agents useful in preparing sulfonated amino acids include sulfonating agents having the formula R$^{30}$—SO$_2$—X wherein R$^{30}$ is an appropriate group for the modified non-α-amino acid, poly amino acid, or peptide being prepared such as, but not limited to, alkyl, alkenyl, cycloalkyl, or aromatics and X is a leaving group as described above. One example of a sulfonating agent is benzene sulfonyl chloride.

Emulsification Methods

In forming an emulsion, the aqueous and non-aqueous phases are combined in the presence of an emulsifier and are mixed. The mixing can be performed by shaking, mechanical blending, sonication, or any other method known in the art. A preferred method is mechanical blending, such as, for example, mixing in a blender, stirring with an overhead stirrer, or vortexing.

Mechanical blenders useful for practicing the present invention include overhead stirrers, such as, for example, a T-Line Laboratory stirrer, model 138, available from TAL-BOYS Engineering, (Emerson, N.J.), or a two speed Waring commercial blender available from Waring Corp. (New Hartford, Conn.). Vortex mixing can be accomplished using, for example, a Vortex Genie-2 mixer available from VWR Scientific (Piscataway, N.J.). Sonication can be performed with a Tekmar Sonic Disruptor available from Tekmar Co. (Cincinnati, Ohio).

The rate of mixing with an overhead stirrer is typically from about 100 to about 500 rpm. A preferred rate is about 300 rpm. When mixing with a blender, a preferred speed is low and when mixing with a Vortex Genie-2, the setting used is 9. Sonication carried out with the Tekmar Sonic Disruptor preferably is at a setting of about 5, and a microtip in continuous (non-pulsed) mode.

Another method for preparing emulsions utilizes the SanSurf™ method, a process performed by Collaborative Laboratories, (East Setauket, N.Y.). In this process the materials are mixed under high pressure and high sheer conditions. This process is produces emulsions having particles of less than 1 μm.

A mixer believed to be useful for the high pressure/high sheer blending in a Microfluridizer Model 110T, available from Microfluridizer Corp., (Newton, Mass.).

The time required for mixing is variable and depends on the method of mixing. Typical times range from about 1 minute for high speed mixing with a blender or vortex mixer to about 1 hour or more when using an overhead stirrer. Sonication typically requires from about 5 to about 20 minutes.

The emulsifier can be added to the mixture at any time prior to or during mixing. The emulsifier can be added to either the aqueous phase, the non-aqueous phase, or to a mixture of the aqueous and the non-aqueous phases.

The level of emulsifier required can range from about 1 weight percent to about 15 weight percent, based on 100 parts by weight of said emulsion. The preferred amount of emulsifier is from about 4 to about 8 weight percent.

DESCRIPTION OF THE PREFERRED EMBODIMENTS

The following examples are illustrative of the invention but are not intended to limit the scope of the invention.

EXAMPLE 1

Five grams of benzoyl modified hydrolyzed soy protein were dissolved in 50 mL of water to form a 5% by weight solution of modified hydrolyzed vegetable protein. The pH of the solution was adjusted to within a range from about 5 to about 7.5. Vinyl acetate monomer (50 mL) was stirred into the modified hydrolyzed vegetable protein/water solution using an overhead stirring device, at about 300 rpm. The final volume ratio of water:monomer was 1:1. One hour after the monomer was added, the agitation was stopped, yielding an emulsion that remained stable for over 6 hours.

EXAMPLE 2

Five grams of cyclohexanoyl modified hydrolyzed soy protein were dissolved in 50 mL of water to form a 5% by weight solution of modified hydrolyzed vegetable protein. The pH of the solution was adjusted to within a range from about 5 to about 7.5. Vinyl acetate monomer (50 mL) was stirred at high agitation into the modified hydrolyzed vegetable protein/water solution using an overhead stirring device, at about 300 rpm. The final volume ratio of water:monomer was 1:1. One hour after the monomer was added, the agitation was stopped, yielding an emulsion that remained stable for over 6 hours.

EXAMPLE 3

Five grams of phthaloyl modified hydrolyzed soy protein were dissolved in 50 mL of water to form a 50% by weight solution of modified hydrolyzed vegetable protein. The pH of the solution was adjusted to within a range from about 5 to about 7.5. Vinyl acetate monomer (50 mL) was added and stirred at high agitation with the modified hydrolyzed vegetable protein/water solution using an overhead stirring device, at about 300 rpm. The volume ratio of water:monomer was 1:1. The agitation was stopped, after one hour yielding an emulsion that remained stable for over 6 hours.

EXAMPLE 4

Five grams of benzene sulfonyl modified hydrolyzed soy protein were dissolved in 50 mL of water to form a 5% by weight solution of modified hydrolyzed vegetable protein. The pH of the solution was adjusted to within a range from about 5 to about 7.5. Vinyl acetate monomer (50 mL) was stirred at high agitation into the modified hydrolyzed vegetable protein/water solution using an overhead stirring device, at about 300 rpm. The final volume ratio of water:monomer was 1:1. One hour after the monomer was added, the agitation was stopped, yielding an emulsion that remained stable for over 6 hours.

EXAMPLE 5

Five grams of tetrahydrophthaloyl modified hydrolyzed soy protein were dissolved in 50 mL of water to form a 5% by weight solution of modified hydrolyzed vegetable protein. The pH of the solution was adjusted to within a range from about 5 to about 7.5. Vinyl acetate monomer (50 mL) was stirred at high agitation into the modified hydrolyzed vegetable protein/water solution using an overhead stirring device, at about 300 rpm. The final volume ratio of water:monomer was 1:1. One hour after the monomer was added, the agitation was stopped, yielding an emulsion that remained stable for over 6 hours.

EXAMPLE 6

Five grams of benzoyl modified hydrolyzed soy protein were dissolved in 50 mL of water to form a 5% by weight solution of modified hydrolyzed vegetable protein. The pH of the solution was adjusted to within a range from about 5 to about 7.5. A monomer mixture of butyl acrylate and methyl methacrylate (50:50) (50 mL) was stirred into the modified hydrolyzed vegetable protein/water solution using an overhead stirring device, at about 300 rpm. The final volume ratio of water:dual monomer was 1:1. One hour after the monomer was added, the agitation was stopped, yielding an emulsion that remained stable for over 24 hours.

EXAMPLE 7

Five grams of cyclohexanoyl modified hydrolyzed soy protein were dissolved in 50 mL of water to form a 5% by weight solution of modified hydrolyzed vegetable protein. The pH of the solution was adjusted to within a range from about 5 to about 7.5. A monomer mixture of butyl acrylate and methyl methacrylate (50:50) (50 mL) was stirred into the modified hydrolyzed vegetable protein/water solution using an overhead stirring device, at about 300 rpm. The final volume ratio of water:dual monomer was 1:1. One hour after the monomer was added, the agitation was stopped, yielding an emulsion that remained stable for over 6 hours.

EXAMPLE 8

Five grams of phthaloyl modified hydrolyzed soy protein were dissolved in 50 mL of water to form a 5% by weight solution of modified hydrolyzed vegetable protein. The pH of the solution was adjusted to within a range from about 5 to about 7.5. A monomer mixture of butyl acrylate and methyl methacrylate (50:50) (50 mL) was stirred into the modified hydrolyzed vegetable protein/water solution using an overhead stirring device, at about 300 rpm. The final volume ratio of water:dual monomer was 1:1. One hour after the monomer was added, the agitation was stopped, yielding an emulsion that remained stable for over 6 hours.

EXAMPLE 9

Five grams of benzene sulfonyl modified hydrolyzed soy protein were dissolved in 50 mL of water to form a 5% by weight solution of modified hydrolyzed vegetable protein. The pH of the solution was adjusted to within a range from about 5 to about 7.5. A monomer mixture of butyl acrylate and methyl methacrylate (50:50) (50 mL) was stirred into the modified hydrolyzed vegetable protein/water solution using an overhead stirring device, at about 300 rpm. The final volume ratio of water:dual monomer was 1:1. One hour after the monomer was added, the agitation was stopped, yielding an emulsion that remained stable for over 6 hours.

EXAMPLE 10

Five grams of tetrahydrophthaloyl modified hydrolyzed soy protein were dissolved in 50 mL of water to form a 5% by weight solution of modified hydrolyzed vegetable protein. The pH of the solution was adjusted to within a range from about 5 to about 7.5. A monomer mixture of butyl acrylate and methyl methacrylate (50:50) (50 mL) was stirred into the modified hydrolyzed vegetable protein/water solution using an overhead stirring device, at about 300 rpm. The final volume ratio of water:dual monomer was 1:1. One hour after the monomer was added, the agitation was stopped, yielding an emulsion that remained stable for over 6 hours.

EXAMPLE 11

Ten grams of hexahydrophthaloyl modified hydrolyzed soy protein were dissolved in 100 mL of a 1.7 N aqueous citric acid solution having 1% gum acacia to form a 10% by weight solution of modified hydrolyzed vegetable protein. The pH of the solution was adjusted to about 7.5. Limonene (1.0 g) was combined with the modified hydrolyzed vegetable protein/water solution and mixed, for about 1 minute, using a Waring commercial blender at low speed. This yielded a stable emulsion.

EXAMPLE 12

Five grams of N-cyclohexanoyl-6-aminohexanoic acid were dissolved in 50 mL of water to form a 50 by weight solution of modified amino acid. The pH of the solution was adjusted to within a range from about 5 to about 7.5. Vinyl acetate monomer (50 mL) was stirred into the modified hydrolyzed vegetable protein/water solution using an overhead stirring device, at about 300 rpm. The final volume ratio of water:monomer was 1:1. One hour after the monomer was added, the agitation was stopped, yielding an emulsion that remained stable for over 24 hours.

EXAMPLE 13

A proteinoid having the molar composition Glu-Asp-0.4Lys-Phe (20 mg) was dissolved in water (20 mL) and 2.0 mL of heptane was added. The mixture was mixed for 1 minute with a vortex mixer. This yielded an emulsion that remained stable stable for over 72 hours.

EXAMPLE 14

A proteinoid having the molar composition Glu-Asp-0.4Lys-Phe (20 mg) was dissolved in water (20 mL) and 2.0 mL of mesitylene was added. The mixture was mixed for 1 minute with a vortex mixer. This yielded an emulsion that remained stable for over 72 hours.

EXAMPLE 15

A proteinoid having the molar composition Glu-Asp-Tyr-Phe-0.50rn (20 mg) was dissolved in water (20 mL) and 2.0 mL of heptane was added. The mixture was mixed for 1 minute with a vortex mixer. This yielded an emulsion that remained stable for over 96 hours.

EXAMPLE 16

A proteinoid having the molar composition Glu-Asp-Tyr-Phe-0.50rn (20 mg) was dissolved in water (20 mL) and 2.0 mL of mesitylene was added. The mixture was mixed for 1 minute with a vortex mixer. This yielded an emulsion that remained stable for over 96 hours.

EXAMPLE 17

A proteinoid having the molar composition Glu-Asp-Tyr-Phe-0.50rn (20 mg) was dissolved in water (20 mL) and 2.0 mL of diethyl phthalate was added. The mixture was mixed for 1 minute with a vortex mixer. This yielded an emulsion that remained stable for over 96 hours.

EXAMPLE 18

A proteinoid having the molar composition Glu-Asp-Tyr-Phe-0.50rn (20 mg) was dissolved in water (20 mL) and 2.0 mL of soy oil was added. The mixture was mixed for 1 minute 6 with a vortex mixer. This yielded an emulsion that remained stable for over 72 hours.

EXAMPLE 19–26

Following the procedures described in the Examples hereinabove emulsions were prepared. The results are summarized in Table I.

TABLE I

| EXAMPLE NO. | EMULSIFIER | NON-AQUEOUS PHASE |
| --- | --- | --- |
| 19 | Acetylsulfanilyl modified soy protein | Vinyl Acetate |
| 20 | Acetylsulfanilyl modified soy protein | Butyl Acrylate/ Methyl Methacrylate |
| 21 | Hexahydrophthaloyl modified soy protein | Vinyl Acetate |
| 22 | Hexahydrophthaloyl modified soy protein | Butyl Acrylate/ Methyl Methacrylate |
| 23 | Maleoyl modified soy protein | Vinyl Acetate |
| 24 | Maleoyl modified soy protein | Butyl Acrylate/ Methyl Methacrylate |
| 25 | Sebacoyl modified soy protein | Vinyl Acetate |
| 26 | Benzoyl modified soy protein | Butyl Acrylate/ Methyl Methacrylate |

EXAMPLE 27

Ten grams of hexahydrophthaloyl modified hydrolyzed soy protein were dissolved in 100 mL of water to form a 10% by weight solution of modified hydrolyzed vegetable protein. The pH of the solution was adjusted to within a range from about 7.3 to about 7.8 by addition of 10 N NaOH. A portion of this solution (50 mL) and limonene (20 mL) were combined and mixed using an overhead stirring device, at about 300 rpm. One hour after the limonene was added, the agitation was stopped, yielding an emulsion that remained stable for over 6 hours.

EXAMPLE 28

A proteinoid having the molar composition, Glu-Asp-0.4Lys-Phe was dissolved in water at a concentration of 10 g/L (1%). Vegetable oil (soy) was added at a concentration of 10% (v/v). The mixture was blended under high pressure and high sheer conditions. A stable emulsion was produced. Dark field light microscopic images of these emulsions are illustrated in FIGS. 1 and 2.

EXAMPLE 29

A proteinoid having the molar composition, Glu-Asp-2Arg-Phe was dissolved in water at a concentration of 10 g/L. Vegetable oil (soy) was added at a concentration of 10% (v/v). The mixture was blended under high pressure and high sheer conditions. A stable emulsion was produced.

All patents, applications, test methods, and publications mentioned herein are hereby incorporated by reference.

Many variations of the present invention will suggest themselves to those skilled in the art in light of the above detailed disclosure. All such variations are within the full intended scope of the appended claims.

What is claimed is:

1. An emulsion comprising
   (A) an aqueous phase;
   (B) an non-aqueous phase; and
   (C) (i) a mixed amino acid proteinoid emulsifier;
      (ii) a modified hydrolyzed vegetable protein emulsifier wherein said modified hydrolyzed vegetable protein is modified with an amine reactive modifying agent;
      (iii) an acylated non-α-amino acid emulsifier;
      (iv) an acylated poly amino acid emulsifier;
      (v) an acylated peptide emulsifier;
      (vi) a sulfonated non-α-amino acid emulsifier;
      (vii) a sulfonated poly amino acid emulsifier;
      (viii) a sulfonated peptide emulsifier; or
      (ix) any combination of (i), (ii), (iii), (iv), (v), (vi), (vii) and (viii).

2. The emulsion of claim 1, wherein said non-aqueous phase comprises an oil.

3. The emulsion of claim 2, wherein said emulsion is selected from the group consisting of an oil-in-water emulsion and a water-in-oil emulsion.

4. The emulsion of claim 2, wherein said non-aqueous phase comprises soy oil.

5. The emulsion of claim 1, wherein said non-aqueous phase comprises a composition comprising at least one vinyl monomer.

6. The emulsion of claim 5, wherein said vinyl monomer is selected from the group consisting of vinyl acetate, butyl acrylate, methyl methacrylate, and a mixture of any of the foregoing.

7. The emulsion of claim 1, wherein said mixed amino acid proteinoid emulsifier is a linear proteinoid of mixed amino acids.

8. The emulsion of claim 1, wherein said mixed amino acid proteinoid emulsifier comprises a condensation polymer of mixed amino acids.

9. The emulsion of claim 8, wherein said mixed amino acid proteinoid emulsifier comprises a thermal condensation polymer of mixed amino acids.

10. The emulsion of claim 8, wherein said mixed amino acid proteinoid emulsifier comprises a directed condensation polymer of mixed amino acids.

11. The emulsion of claim 8, wherein said mixed amino acid proteinoid emulsifier comprises a random condensation polymer of mixed amino acids.

12. The emulsion of claim 1, wherein said mixed amino acid proteinoid emulsifier comprises a diketopiperazine.

13. The emulsion of claim 1, wherein said mixed amino acid proteinoid emulsifier has a molecular weight ranging from about 250 to about 2400.

14. The emulsion of claim 13, wherein said mixed amino acid proteinoid emulsifier has a molecular weight ranging from about 250 to about 400.

15. The emulsion of claim 1, wherein said mixed amino acid proteinoid emulsifier comprises from about 2 to about 20 amino acids.

16. The emulsion of claim 15, wherein said mixed amino acid proteinoid emulsifier has from about 2 to about 8 amino acids.

17. The emulsion of claim 1, wherein said mixed amino acid proteinoid emulsifier comprises an acid-soluble proteinoid.

18. The emulsion of claim 1, wherein said mixed amino acid proteinoid emulsifier comprises a base-soluble proteinoid.

19. The emulsion of claim 7, wherein said mixed amino acid proteinoid emulsifier is selected from the group consisting of Glu-Asp-2Arg-Phe, Glu-Asp-Tyr-Phe-0.5Orn, and Glu-Asp-0.4Lys-Phe.

20. The emulsion of claim 1, wherein said modified hydrolyzed vegetable protein emulsifier comprises acid hydrolyzed soybean protein.

21. The emulsion of claim 1, wherein said amine reactive modifying group is selected from the group consisting of a benzene sulfonyl group, a benzoyl group, a phthaloyl group, a tetrahydrophthaloyl group, and a cyclohexanoyl group.

22. The emulsion of claim 1, wherein said acylated non-$\alpha$-amino acid is N-cyclohexanoyl-6-aminohexanoic acid.

23. The emulsion of claim 1, comprising from about 1 to about 15 percent by weight of emulsifier, based on 100 parts by weight of said emulsion.

24. The emulsion of claim 23, comprising from about 4 to about 8 percent by weight of emulsifier, based on the 100 parts by weight of said emulsion.

25. The emulsion of claim 1, wherein said mixed amino acid proteinoid emulsifier is a branched proteinoid of mixed amino acids.

26. The emulsion of claim 1, wherein said mixed amino acid proteinoid emulsifier is a cyclic proteinoid of mixed amino acids.

* * * * *